(12) United States Patent
Breton et al.

(10) Patent No.: US 6,264,962 B1
(45) Date of Patent: Jul. 24, 2001

(54) USE OF CINNAMIC ACID OR OF AT LEAST ONE OF ITS DERIVATIVES IN A COSMETIC COMPOSITION

(75) Inventors: Lionel Breton, Versailles; Florence Girerd, Paris; Béatrice Renault, Saint Maurice, all of (FR)

(73) Assignee: Societe l'Oreal S.A., Paris (FR)

( * ) Notice: Subject to any disclaimer, the term of this patent is extended or adjusted under 35 U.S.C. 154(b) by 0 days.

(21) Appl. No.: 09/216,868

(22) Filed: Dec. 21, 1998

(30) Foreign Application Priority Data

Dec. 19, 1997 (FR) .................................................. 97 16178

(51) Int. Cl.$^7$ ............................... A61K 7/00; A61K 6/00
(52) U.S. Cl. ........................ 424/401; 514/969; 514/846
(58) Field of Search ............................ 424/401; 514/969, 514/846

(56) References Cited

U.S. PATENT DOCUMENTS

| | | |
|---|---|---|
| 4,466,961 | 8/1984 | Szijjarto nee Auber et al. . |
| 5,093,109 | 3/1992 | Mausner . |
| 5,536,500 * | 7/1996 | Galey et al. .................. 424/401 |
| 5,837,697 * | 11/1998 | Blank et al. .................. 514/159 |
| 5,952,373 | 9/1999 | Lanzendorfer et al. . |

FOREIGN PATENT DOCUMENTS

| | | |
|---|---|---|
| 0 103 878 A2 | 9/1983 | (EP) . |
| 0664290 | 7/1995 | (EP) . |
| 0716847 | 6/1996 | (EP) . |
| 1 269 573 | 6/1959 | (FR) . |
| 2 315 908 | 1/1977 | (FR) . |
| 57-167921 | 10/1982 | (JP) . |
| 63-277615 | 11/1988 | (JP) . |
| 64-13018 | 1/1989 | (JP) . |
| 0 451 889 A1 | 10/1991 | (JP) . |
| 5-78230 | 3/1993 | (JP) . |
| 5-105621 | 4/1993 | (JP) . |
| 5-105643 | 4/1993 | (JP) . |
| 5-221845 | 8/1993 | (JP) . |
| 5-310526 | 11/1993 | (JP) . |
| 6-321754 | 11/1994 | (JP) . |
| 7-300-469 | 11/1995 | (JP) . |
| 8-12664 | 1/1996 | (JP) . |
| 8-259421 | 10/1996 | (JP) . |
| 9-124474 | 5/1997 | (JP) . |
| 9-132527 | 5/1997 | (JP) . |
| 11-246328 | 9/1999 | (JP) . |
| 11-246333 | 9/1999 | (JP) . |
| 92/07544 | 5/1992 | (WO) . |
| 99/32078 | 7/1999 | (WO) . |

OTHER PUBLICATIONS

Database WPI, Week 8936, Derwent Publications Ltd., London, AN 89–258961.
W.A. Poucher: "Poucher's Perfumes . . . ", Cosmetics & Soaps, vol. 1.
P. Rovesti, "Recherches sur l'action . . . ", Parfumerie Mod., vol. 48, No. 54, 1956.
Database WPI, Week 8802 XP002081837, "Hair rinsing . . . ".
Patent Abstracts of Japan, vol. 017, No. 674, Dec. 10, 1993.
Patent Abstracts of Japan, vol. 018, No. 118, Feb. 25, 1994.
English abstract of JP 9132527.
English abstract of EP 0 103 878.
Claims of JP 63–277615 (In French).
English abstract of Japanese 5–221845.
English abstract of EP 0506961.
English abstract of Japanese 5–310526.
English abstract of JP 1013018.
English abstract of JP 5–78230.
English abstract of JP 5–105621.
English abstract of JP 5–105643.
English abstract of JP 6–321754.
English abstract of JP 9–124474.

* cited by examiner

Primary Examiner—Thurman K. Page
Assistant Examiner—Todd D Ware
(74) Attorney, Agent, or Firm—Burns, Doane, Swecker & Mathis, L.L.P.

(57) ABSTRACT

The invention relates to the use of cinnamic acid, or of at least one of its derivatives, in a cosmetic composition as an agent for promoting the synthesis of the skin's total lipids.

The invention also relates to a cosmetic composition comprising an effective amount of cinnamic acid or of at least one of its derivatives.

22 Claims, No Drawings

USE OF CINNAMIC ACID OR OF AT LEAST ONE OF ITS DERIVATIVES IN A COSMETIC COMPOSITION

The invention relates to the use of cinnamic acid, or of at least one of its derivatives, in a cosmetic composition as an agent for promoting the synthesis of skin lipids.

In particular, the compositions of the invention are intended to stimulate the synthesis of the skin's total lipids, particularly those of the epidermis.

The invention also relates to a cosmetic composition comprising an effective amount of cinnamic acid or of at least one of its derivatives.

Human skin consists of two compartments, i.e. a deep compartment, the dermis, and a superficial compartment, the epidermis.

The dermis gives the epidermis a solid support. It is also the epidermis' nourishing factor. It consists mainly of fibroblasts and of an extracellular matrix composed mainly of collagen, elastin and a substance known as ground substance, these components being synthesized by the fibroblasts. Leukocytes, mastocytes and tissue macrophages are also found therein. It also contains blood vessels and nerve fibres.

The epidermis is in contact with the external environment. Its role consists in protecting the body against dehydration and external attack, whether of chemical, mechanical, physical or infectious nature.

Natural human epidermis is composed mainly of three types of cells: the keratinocytes, which form the great majority, the melanocytes and the Langerhans cells. Each of these cell types contributes, by virtue of its intrinsic functions, towards the essential role played in the body by the skin.

The cells constituting the epidermis are bounded by an intercellular lipid region. During differentiation, phospholipids, whose role consists in developing the fluid structure of the cell membranes of the live layers of the epidermis, are gradually replaced by a mixture composed mainly of fatty acids, cholesterol and sphingolipids.

These lipids are organized into specific lamellar structures whose integrity depends not only on the quality of the fractions present but also on their respective proportion. This lamellar structure of the lipids in the intercellular lipid region of the epidermis is responsible for the skin's fluidity, and thus its suppleness.

The lipids are also responsible for the "barrier" properties of the epidermis, particularly of the stratum corneum.

The epidermal lipids are mainly synthesized in the live epidermis. They consist mainly of phospholipids, sphingolipids, cholesterol, free fatty acids, triglycerides, cholesterol esters and alkanes.

Phospholipids are essential for making up cell membranes. They play an important role in mediating extracellular signals and in forming free aliphatic chains used for the production of energy. They constitute a reserve of free fatty acids needed to make up the sphingolipids.

Sphingolipids (or ceramides) are essential for maintaining the multilamellar structure of the intercorneocytic lipids. They are also essential for water exchanges and for the "barrier" function of the epidermis.

Cholesterol plays a prime role in moisturization of the skin and in the "barrier" function of the epidermis.

Free fatty acids play a major role in maintaining the lamellar structure of the lipids in the stratum corneum, but also in making up cell membranes in which they are responsible for the membrane fluidity as well as for physiological processes such as the functioning of receptors or enzymatic activity.

The essential role played by skin lipids and the importance which their integrity entails can thus be appreciated.

It is known, unfortunately, that the lipids in the skin, particularly in the epidermis, are influenced by genetic factors, ageing, dietary habits, the seasons, environmental factors, external attack and/or certain pathologies (for example scurvy or pellagra). The consequence of all these factors is to adversely affect or modify the composition of the skin lipids or to decrease the amount therein, which invariably leads to dry skin. It is known, for example, that the absence of the lipid component in a diet has the consequence of skin in a poor state of health. The absence of lipids leads to general deterioration of the state of health and particularly to the appearance of flaky skin which increases as the trans-epidermal loss of water increases.

The skin's lipids are thus essential in maintaining the skin's water "barrier".

It is also known that the lipids in the epidermis also have an influence on the activity of certain skin enzymes involved in the maturation and desquamation of the stratum corneum.

Variations in the levels and types of lipids present in the stratum corneum thus influence the "barrier" function of the stratum corneum, the water content and the condition of the skin.

It is also known that during the menopause women complain that their skin feels tight and that it takes on the appearance of "dry skin", or even the appearance of xerosis. Without wishing to establish any particular theory, given that the skin lipids play an important role in moisturizing the skin and that the hormonal deficiencies associated with the menopause are accompanied by a general slowing-down in cell metabolism, it can nevertheless be assumed that the sensation of tightness of the skin or of dry skin which is experienced by women is linked in particular to a decrease in the amount of total lipids in the skin.

It can thus be appreciated that it is important to be able to stimulate the synthesis of skin lipids in order to maintain and/or restore their integrity, so as to allow them to carry out the important roles for which they are responsible.

In this regard, the Applicant has discovered, surprisingly and unexpectedly, that cinnamic acid or its derivatives have the property of stimulating the synthesis of lipids, particularly the skin's total lipids.

Cinnamic acid is present in trans form in the essential oils of basil or of cinnamon, in Peruvian balsam and in cocoa leaves. The cis form is present in the oil from *Alpinia malacensis*.

In the prior art, cinnamic acid or its derivatives are known to be used in compositions for preventing bedsores (JP 07 242 558), as an anti-ultraviolet active agent (U.S. Pat. No. 5,093,109), in permanent-waving compositions (DE 3,301,515, DE 2,912,477 and EP 22,996), in hair lotions (JP 7,053,401 and JP 3,041,413), in depigmenting compositions (JP 5,221,845 and JP 1,186,811) and as antioxidant (EP 664,290).

To the Applicant's knowledge, the use of cinnamic acid or of its derivatives to stimulate the synthesis of the skin's total lipids has never been described in the prior art.

The subject of the invention is thus the use, in a cosmetic composition, of an effective amount of cinnamic acid or of at least one of its derivatives, the cinnamic acid or the composition being intended to stimulate the synthesis of the skin's total lipids.

The cinnamic acid or its derivatives can be of natural or synthetic origin. The term natural origin refers to cinnamic acid, or its derivatives, prepared from plant material in which they are found in the natural state. The term synthetic origin refers to cinnamic acid, or its derivatives, prepared by chemical synthesis or by biotechnology.

Thus, in the text hereinbelow, the term cinnamic acid is understood to denote cinnamic acid, or its derivatives, of natural or synthetic origin, in purified form or any preparation containing them.

Among the cinnamic acid derivatives which can be used according to the invention, mention may be made, for example, of mono- and polyhydroxycinnamic acids, alcohols, aldehydes, esters and derivatives.

Cinnamic acid is preferably used according to the invention.

Needless to say, it is possible according to the invention to use cinnamic acid or its derivatives alone or as a mixture.

It has been seen above that the lipids are involved, inter alia, in the skin's barrier function, in moisturization of the skin and in the suppleness of the skin. It has also been seen that the menopause induces effects on the skin, more particularly on the skin lipids.

Hence, one of the aspects of the invention is thus to propose the use, in a cosmetic composition, of an effective amount of cinnamic acid or of at least one of its derivatives, the cinnamic acid or the composition being intended to reinforce the skin's barrier function.

According to another aspect, the subject of the invention is the use, in a cosmetic composition, of an effective amount of cinnamic acid or of at least one of its derivatives, the cinnamic acid or the composition being intended to promote moisturization of the skin.

According to yet another aspect, the subject of the invention is the use, in a cosmetic composition, of an effective amount of cinnamic acid or of at least one of its derivatives, the cinnamic acid or the composition being intended to reinforce the suppleness of the skin.

According to yet another aspect, the subject of the invention is the use, in a cosmetic composition, of an effective amount of cinnamic acid or of at least one of its derivatives, the cinnamic acid or the composition being intended to combat the effects of the menopause on the skin.

Lastly, according to another aspect, the subject of the invention is the use, in a cosmetic composition, of an effective amount of cinnamic acid or of at least one of its derivatives, the cinnamic acid or the composition being intended to combat the effects of the menopause on the skin lipids.

The amount of cinnamic acid, or of its derivatives, which can be used according to the invention obviously depends on the desired effect and must be in an amount which is effective for stimulating the synthesis of the skin lipids.

For example, the amount of cinnamic acid which can be used according to the invention can range, for example, from $10^{-6}\%$ to 10% and preferably from $10^{-3}\%$ to 5% of the total weight of the composition.

It is possible in the invention to use the cinnamic acid or one of its derivatives in combination with another product which stimulates lipid synthesis. Among these other products which stimulate lipid synthesis, mention may be made of plant hormones.

Among the plant hormones, mention may be made of auxins such as 3-indoleacetic acid (IAA), 4-chloro-3-indoleacetic acid (4-Cl-IAA), phenylacetic acid (PAA), 3-indolebutyric acid (IBA), 2,4-dichlorophenoxyacetic acid (2,4-D), α-naphthaleneacetic acid (α-NAA), β-naphthoxyacetic acid, indolethanol, indoleacetaldehyde and indoleacetonitrile.

β-Naphthoxyacetic acid is preferably used according to the invention.

Since the skin is made up of many components other than lipids, it turns out to be advantageous, when synthesis of the skin is promoted with cinnamic acid, to simultaneously promote the synthesis of these other components such as, for example, collagen.

Thus, it is also possible in the invention to use the cinnamic acid or one of its derivatives in combination with another product which, for example, stimulates collagen synthesis.

In this regard, plant hormones such as auxins, and particularly β-naphthoxyacetic acid can also be mentioned.

The subject of the invention is also a cosmetic composition intended to promote the synthesis of the skin's total lipids, comprising, in a cosmetically acceptable medium, an effective amount of cinnamic acid or of one of its derivatives.

The product which stimulates the synthesis of lipids and/or of collagen can be used in an amount of between $10^{-6}\%$ and 10%, and preferably between $10^{-3}\%$ and 5%, of the total weight of the composition.

The subject of the invention is also a moisturizing cosmetic composition comprising, in a cosmetically acceptable medium, an effective amount of cinnamic acid or of one of its derivatives.

The subject of the invention is also a supplying cosmetic composition comprising, in a cosmetically acceptable medium, an effective amount of cinnamic acid or of one of its derivatives.

The subject of the invention is also a cosmetic composition intended to reinforce the skins "barrier" function, comprising, in a cosmetically acceptable medium, an effective amount of cinnamic acid or of one of its derivatives.

Lastly, the subject of the invention is a cosmetic composition intended to combat the effects of the menopause on the skin, particularly the effects of the menopause on skin lipids, comprising, in a cosmetically acceptable medium, an effective amount of cinnamic acid or of one of its derivatives.

The term cosmetically acceptable medium refers to a medium which is compatible with the skin, the scalp, mucous membranes, the nails and the hair.

Needless to say, the composition according to the invention comprises a cosmetically acceptable support and can be in any pharmaceutical form normally used for topical application, in particular in the form of an aqueous, aqueous-alcoholic or oily solution, an oil-in-water, water-in-oil or multiple emulsion, an aqueous or oily gel, a liquid, pasty or solid anhydrous product, a dispersion of oil in an aqueous phase using spherules, it being possible for these spherules to be polymer nanoparticles such as nanospheres and nanocapsules or, better still, lipid vesicles of ionic and/or nonionic type.

This composition can be more or less fluid and can have the appearance of a white or coloured cream, an ointment, a milk, a lotion, a serum, a paste or a mousse. It can optionally be applied to the skin in the form of an aerosol. It can also be in solid form and, for example, in the form of a stick. It can be used as a care product, as a cleansing product, as a make-up product or as a simple deodorant product.

In a known manner, the composition according to the invention can also contain adjuvants which are common in the cosmetic and dermatological fields, such as hydrophilic or lipophilic gelling agents, hydrophilic or lipophilic active agents, preserving agents, antioxidants, solvents, fragrances, fillers, screening agents, pigments, chelating agents, odour absorbers and dyestuffs. The amounts of these various adjuvants are those used conventionally in the fields considered, and, for example, from 0.01% to 20% of the total weight of the composition. Depending on their nature, these adjuvants can be introduced into the fatty phase, into the aqueous phase, into the lipid vesicles and/or into the nanoparticles.

When the composition of the invention is an emulsion, the proportion of the fatty phase can range from 5% to 80% by weight, and preferably from 5% to 50%, of the total weight of the composition. The oils, the emulsifiers and the co-emulsifiers used in the composition in emulsion form are chosen from those used conventionally in the field considered. The emulsifier and the co-emulsifier are present in the composition in a proportion ranging from 0.3% to 30% by weight, and preferably from 0.5% to 20%, of the total weight of the composition.

As oils which can be used in the invention, mention may be made of mineral oils, oils of plant origin (apricot oil, sunflower oil), oils of animal origin, synthetic oils, silicone oils and fluoro oils (perfluoropolyethers). Fatty alcohols (cetyl alcohol), fatty acids and waxes (beeswax) can also be used as fatty substances.

As emulsifiers and co-emulsifiers which can be used in the invention, mention may be made, for example, of fatty acid esters of polyethylene glycol, such as PEG-40 stearate and PEG-100 stearate, and fatty acid esters of polyols, such as glyceryl stearate and sorbitan tristearate.

As hydrophilic gelling agents, mention may be made in particular of carboxyvinyl polymers (carbomer), acrylic copolymers such as acrylate/alkylacrylate copolymers, polyacrylamides, polysaccharides, natural gums and clays, and, as lipophilic gelling agents, mention may be made of modified clays such as bentones, metal salts of fatty acids, hydrophobic silica and polyethylenes.

The composition can contain other hydrophilic active agents such as proteins or protein hydrolysates, amino acids, polyols, urea, allantoin, sugars and sugar derivatives, water-soluble vitamins, plant extracts and hydroxy acids.

Retinol (vitamin A) and its derivatives, tocopherol (vitamin E) and its derivatives, essential fatty acids, ceramides, essential oils and salicylic acid and its derivatives can be used as lipophilic active agents.

It is also possible according to the invention to use, in combination with the cinnamic acid or at least one of its derivatives, compounds chosen from plant hormones;

antibacterial agents such as macrolides, pyranosides and tetracyclines, and in particular erythromycin;

calcium antagonists such as verapamil and diltiazem;

OH radical scavengers such as dimethyl sulphoxide;

plant extracts such as those from Iridaceae or from soybean, these extracts also possibly containing isoflavones;

extracts from microorganisms including, in particular, bacterial extracts such as those from non-photosynthetic filamentous bacteria.

Other compounds can also be added to the above list, namely, for example, potassium-channel openers such as diazoxide and minoxidil, spiroxazone, phospholipids such as lecithin, linoleic and linolenic acids, salicylic acid and its derivatives described in French patent FR 2,581,542, such as salicylic acid derivatives bearing an alkyl group containing from 2 to 12 carbon atoms in position 5 of the benzene ring, hydroxycarboxylic or ketocarboxylic acids and their esters, lactones and their corresponding salts, anthralin, carotenoids, eicosatetraenoic and eicosatrienoic acids or their esters and amides, and vitamin D and its derivatives.

According to the invention, it is possible, inter alia, to combine cinnamic acid or at least one of its derivatives with other active agents intended in particular for preventing and/or treating skin complaints. Among these active agents, mention may be made, for example of:

agents which modify skin differentiation and/or proliferation and/or pigmentation, such as retinoic acid and its isomers, retinol and its esters, vitamin D and its derivatives, oestrogens such as oestradiol, kojic acid or hydroquinone;

antiparasitic agents, in particular metronidazole, crotamiton or pyrethroids;

antifungal agents, in particular compounds belonging to the imidazole class such as econazole, ketoconazole or miconazole or their salts, polyene compounds such as amphotericin B, compounds of the allylamine family such as terbinafine, or octopirox;

antiviral agents such as acyclovir;

steroidal anti-inflammatory agents such as hydrocortisone, betamethasone valerate or clobetasol propionate, or non-steroidal anti-inflammatory agents such as ibuprofen and its salts, diclofenac and its salts, acetylsalicylic acid, acetaminophen or glycyrrhetinic acid;

anaesthetics such as lidocaine hydrochloride and its derivatives;

anti-pruriginous agents such as thenaldine, trimeprazine or cyproheptadine;

keratolytic agents such as α- and β-hydroxycarboxylic or β-ketocarboxylic acids, their salts, amides or esters, and more particularly hydroxy acids such as glycolic acid, lactic acid, salicylic acid, citric acid and fruit acids in general, and 5-n-octanoylsalicylic acid;

anti-free-radical agents such as α-tocopherol or its esters, superoxide dimutases, certain metal-chelating agents or ascorbic acid and its esters;

anti-seborrhoeic agents such as progesterone;

antidandruff agents such as octopirox or zinc pyrithione;

anti-acne agents such as retinoic acid or benzoyl peroxide;

substances such as antagonists of substance P, of CGRP or of bradykinin or NO synthase inhibitors, compounds described as being active in the treatment of sensitive skin and as having anti-irritant effects, in particular with respect to irritant compounds which may be present in the compositions.

Thus, another subject of the invention relates to a composition comprising an effective amount of cinnamic acid or of at least one of its derivatives and at least one agent chosen from antibacterial agents, antiparasitic agents, antifungal agents, antiviral agents, anti-inflammatories, anti-pruriginous agents, anaesthetics, keratolytic agents, anti-free-radical agents, anti-seborrhoeic agents, antidandruff agents, anti-acne agents, agents for modifying skin differentiation and/or proliferation and/or pigmentation, antagonists of substance P, of CGRP or of bradykinin, or NO synthase inhibitors.

Moisturizers such as polyols (for example glycerol), vitamins (for example D-panthenol), anti-inflammatory agents, calmatives (allantoin, cornflower water), UVA and UVB screening agents, matt-effect agents (for example the partially crosslinked polydimethylorganosiloxanes sold under the name KSG® by Shin Etsu), and mixtures thereof can be used in particular as active agents.

Anti-wrinkle active agents, and in particular tensioning products such as plant proteins and their hydrolysates, in particular the soybean protein extract sold under the name Eleseryl® by the company LSN or the oat derivative sold under the name Reductine® by the company Silab, can also be added.

Needless to say, the cinnamic acid or at least one of its derivatives can be used in the preparation of cosmetic and/or pharmaceutical compositions, particularly dermatological compositions, intended to stimulate lipid synthesis.

Other characteristics and advantages of the invention will emerge more clearly from the examples which follow, which are given as non-limiting illustrations. In the text hereinbelow and hereinabove the proportions are given as a percentage by weight, except where otherwise indicated.

EXAMPLE 1

Study of the effect of cinnamic acid on the synthesis of the skin's total lipids.

The study is carried out by measuring the incorporation of carbon-14-labelled acetate in models of reconstructed human epidermis sold by the company Skinethic, in which the composition of total lipids is close to that of normal human epidermis.

The reconstructed human epidermis cultures are prepared according to the supplier's recommendations.

Cinnamic acid, at concentrations of $10^{-5}$, $10^{-6}$ and $10^{-7}$ M, is placed in contact for 72 hours with reconstructed human epidermes after they have been cultured for 14 days under the conditions recommended by the supplier. The labelling with $^{14}C$ acetate (sodium [$2$-$^{14}C$]-acetate sold by Amersham, 59 mCi/mmol) is carried out 24 hours after placing the test product in contact with the culture, i.e. during the final 48 hours of culturing, at a rate of 0.5 $\mu$Ci of $^{14}C$ acetate per culture.

At the end of culturing, after washing the epidermes with phosphate buffer (PBS), the epidermides are dissociated and the cells are lysed with 0.5 M perchloric acid on ice. The lysates are then extracted with a methanol/chloroform mixture (2:1), centrifuged and the pellets obtained are extracted again under the same conditions as before. The lipids are separated out by addition of PBS and chloroform (Blight-Byer technique). The organic phase containing the lipids is taken off and the radioactive incorporated in this phase is determined by liquid scintillation. The is organic phase is then dried under a stream of nitrogen. Thin layer plate chromatography on Merck K60 plates is carried out using, as eluent, a chloroform/methanol/water mixture (50/18/2.6) to separate the phospholipids, or a hexane/ether/acetic acid mixture (15/5.6/0.19) to separate the neutral lipids.

The plates are then autoradiographed for 24 hours and the chromatograms are analysed by densitometry using the One-D-Scan software from the company Scanalytics.

The results are evaluated relative to a control consisting of cells which have not been treated with cinnamic acid.

A positive control ($10^{-4}$ M trifluoperazine), which is known to stimulate lipid synthesis, and a negative control ($10^{-6}$ M retinoic acid), which is known to inhibit lipid synthesis, are introduced into the test as reference.

The results of this test, expressed as a percentage of stimulation, are presented in the following table.

| Treatment | % |
| --- | --- |
| Untreated cells | 100 |
| $10^{-5}$M cinnamic acid | 113 |
| $10^{-6}$M cinnamic acid | 109 |
| $10^{-7}$M cinnamic acid | 124 |
| $10^{-4}$M trifluoroperazine | 122 |
| $10^{-6}$M retinoic acid | 82 |

These results show that cinnamic acid significantly stimulates the incorporation of $^{14}C$ acetate, showing an effect on lipid synthesis.

EXAMPLE 2

Examples of compositions according to the invention. These compositions are obtained by the usual techniques commonly used in cosmetics or pharmacy.

| | |
| --- | --- |
| Composition 1: Care cream | |
| Beeswax | 1.5% |
| Apricot kernel oil | 13.0% |
| Preserving agents | 0.3% |
| Fragrance | 0.4% |
| β-Naphthoxyacetic acid | 0.01% |
| Cinnamic acid | 0.01% |
| Xanthan | 0.5% |
| Cyclopentadimethylsiloxane | 5.0% |
| Sterilized demineralized water | 69.28% |
| Sucrose mono-di-palmitostearate | 3.0% |
| Methylglucose sesquistearate | 3.0% |
| Stearic acid | 1.0% |
| Cetyl alcohol | 3.0% |
| Composition 2: Body oil | |
| Liquid petroleum jelly | 47.98% |
| Apricot kernel oil | 6.0% |
| Fragrance | 1.0% |
| β-Naphthoxyacetic acid | 0.01% |
| Cinnamic acid | 0.01% |
| Cyclopentadimethylsiloxane | 45.0% |
| Composition 3: Make-up-removing milk | |
| 2-Ethylhexyl palmitate | 10.5% |
| Liquid fraction of karite butter | 16.5% |
| Preserving agents | 0.3% |
| Fragrance | 0.15% |
| β-Naphthoxyacetic acid | 0.01% |
| Cinnamic acid | 0.01% |
| Sodium hydroxide | 0.04% |
| Carboxyvinyl polymer | 0.2% |
| Sterilized demineralized water | 69.79% |
| Mixture of cetylstearylglucoside and of cetyl and stearyl alcohols | 2.5% |
| Composition 4: Care cream | |
| Beeswax | 1.5% |
| Apricot kernel oil | 13.0% |
| Preserving agents | 0.3% |
| Fragrance | 0.4% |
| β-Naphthoxyacetic acid | 0.01% |
| Cinnamic acid | 0.01% |
| Ethyl cinnamate | 0.01% |
| Xanthan | 0.5% |
| Cyclopentadimethylsiloxane | 5.0% |
| Sterilized demineralized water | 69.27% |
| Sucrose mono-di-palmitostearate | 3.0% |
| Methylglucose sesquistearate | 3.0% |
| Stearic acid | 1.0% |
| Cetyl alcohol | 3.0% |

What is claimed is:

1. A method of cosmetic treatment which effects at least one of the following: (i) reinforces the skin's barrier finction, (ii) promotes moisturization of the skin, (iii) reinforces the suppleness of the skin, or (iv) alleviates the effects of menopause on the skin, comprising applying an effective amount of a cosmetic composition comprising an amount of cinnamic acid or a derivative thereof effective to treat at least one of the above, contained in a cosmetically acceptable carrier, wherein the administration of said cinnamic acid or derivative thereof provides for an effective cosmetic treatment by stimulation of skin lipid synthesis.

2. The method of claim 1, wherein said method reinforces the skin's barrier function.

3. The method of claim 1, wherein said method promotes the moisturization of the skin.

4. The method of claim 1, wherein said method enhances the suppleness of the skin.

5. The method of claim 1, wherein said method alleviates the side effects of menopause on the skin.

6. The method of claim 1, wherein said method alleviates the side effects of menopause on the total lipid content of the skin.

7. The method of claim 1, wherein said cosmetic composition is topically applied to the skin of a subject in need of such treatment.

8. The method of claim 1, wherein said cinnamic acid derivatives are selected from the group consisting of mono- and polyhydroxy cinnamic acids, alcohols, aldehydes, esters and derivatives.

9. The method of claim 1, wherein the amount of said cinnamic acid or derivative thereof ranges from $10^{-6}$ percent to 10 percent relative to the total weight of the composition.

10. The method of claim 1, wherein the amount of cinnamic acid or derivative thereof ranges from $10^{-3}$ percent to 5 percent relative to the total weight of the composition.

11. The method of claim 1, wherein said cosmetic composition further comprises at least one other compound which stimulates lipid synthesis.

12. The method of claim 1, wherein said cosmetic composition further comprises at least one other compound which stimulates collagen synthesis.

13. The method of claim 11, wherein said at least one other product which stimulates lipid synthesis is a plant hormone.

14. The method of claim 12, wherein said at least one other product which stimulates collagen synthesis is a plant hormone.

15. The method of claim 13, wherein said plant hormone is an auxin.

16. The method of claim 14, wherein said plant hormone is an auxin.

17. The method of claim 15, wherein said auxin is selected from the group consisting of 3-indoleacetic acid (IAA), 4-chloro-3-indoleacetic acid (4-Cl-IAA), phenylacetic acid (PAA), 3-indolebutyric acid (IBA), 2,4-dichlorophenoxyacetic acid (2,4-D), α-naphthaleneacetic acid (α-NAA), β-naphthoxyacetic acid, indolethanol, indoleacetaldehyde and indoleacetonitrile.

18. The method of claim 16, wherein said auxin is selected from the group consisting of 3-indoleacetic acid (IAA), 4-chloro-3-indoleacetic acid (4-Cl-IAA), phenylacetic acid (PAA), 3-indolebutyric acid (IBA), 2,4-dichlorophenoxyacetic acid (2,4-D), α-naphthaleneacetic acid (α-NAA), β-naphthoxyacetic acid, indolethanol, indoleacetaldehyde and indoleacetonitrile.

19. The method of claim 17, wherein said auxin is β-naphthoxyacetic acid.

20. The method of claim 18, wherein said auxin is β-naphthoxyacetic acid.

21. The method of claim 11, wherein said other compound which stimulates lipid synthesis is contained in an amount ranging from $10^{-6}$ percent to 10 percent by weight.

22. The method of claim 21, wherein the amount of said compound ranges from $10^{-3}$ percent to 5 percent relative to the total weight of the composition.

* * * * *